United States Patent [19]

Paredes-Galvan

[11] 4,016,746
[45] Apr. 12, 1977

[54] SYSTEM AND DETECTOR FOR MEASURING BY MEANS OF SOUND THE LITER WEIGHT OF THE MATERIAL IN SATELLITE COOLERS FOR ROTATIVE OVENS

[76] Inventor: Ricardo Paredes-Galvan, Escobedo sur 733, Ste. 201, Monterrey, Nuevo Leon, Mexico

[22] Filed: July 28, 1975

[21] Appl. No.: 599,885

[52] U.S. Cl. .................................. 73/32 R; 73/69; 73/432 PS
[51] Int. Cl.² .......................................... G01N 9/00
[58] Field of Search ..... 73/32 R, 32 A, 69, 432 PS, 73/552, 73

[56] References Cited
UNITED STATES PATENTS 2,668,365  2/1954  Hogin ................................ 73/32 X
3,050,264  8/1962  Marcyes et al. .................... 73/69 X

FOREIGN PATENTS OR APPLICATIONS 475,421  11/1937  United Kingdom .................. 73/69

Primary Examiner—James J. Gill
Attorney, Agent, or Firm—Laurence R. Brown

[57] ABSTRACT

The present invention refers to a system for measuring by means of sound the liter weight of clinker material which after heat drying in a rotation oven passes to the satellite cooler and it uses a sound level detector producing a graphic measurement of the sound produced by the material situated in the satellite cooler to display the liter weight of said material.

4 Claims, 5 Drawing Figures

SYSTEM AND DETECTOR FOR MEASURING BY MEANS OF SOUND THE LITER WEIGHT OF THE MATERIAL IN SATELLITE COOLERS FOR ROTATIVE OVENS

The present invention refers to a system for measuring by means of sound the litre weight of material which after heat drying in a rotation oven passes to the satellite cooler; more specifically this invention refers to a sound level detector which allows the graphic measurement of the sound produced by the material situated in the satellite cooler to determine accurate by the liter weight of said material and consequently the quality its later use in the manufacture of construction cement.

The purpose of the present invention is to give an adequate and precise means to determine the quality degree of material heat dryed in a rotation oven almost simultaneously with the heat drying process, unlike the procedures known to date in which it is necessary to examine directly the heat dryed material to determine its quality. The latter implies a very important loss of time, since while the physical examination of the material or clinker takes place the heat drying process continues and consequently, if the clinker or material examined is found to be of an unacceptable grade, the entire finished production is lost from the time the examined clinker passed on to the cooler until the time when its quality was determined.

Use of the satellite or planetary coolers with the rotative ovens to produce cement, has displaced the procedure traditionally using coolers of the type with movable grille having cooling fans. The satellite cooler is as deficient in its basic operating concepts, since difficulties in controlling the cooling air used the heat drying process, necessitated other variables such as control of: fuel, current in the oven, the oxygen content in the oven gases and the temperatures of the pre-heater, as well as the visual inspection of the heat drying zone.

The idea of using sound as an auxiliary variable in the operation of the oven came as a result of direct observations made with respect to the different noise levels produced in the cooler caused by materials of different liter weight. That is, with the variations occurring in the heat drying process the material does have uniform weight, hence it was found that by continuously measuring the noise level it could be related to changes in the specific weight of the material processed. The use of the sound level as measure of the liter weight was found to be an excellent aid supplementing the oven current which alone does not react sufficiently to the changes in the process.

From the observations made of different planetary coolers with relation to the sound produced by the material as it comes out of the oven, it was concluded that it is possible to measure the sound, using it as an auxiliary variable in heat drying operation of raw materials in rotative ovens, since the noise level in the cooler varies in a wide gamut between the conditions of a cool oven and a hot oven. The measuring range of the noise level was found to be from 85 to 105 db respectively. These measurements were made by means of analyzing the sound level at a given critical point in the cooler; other measurements taken at different points in the cooler gave varied results.

Once the operation range of the noise level was determined, the values obtained were put on graphs to compare them to the variations occurring with the average value of the oven load (in amperes) with the liter weight being taken each hour. The results obtained were not wholly satisfactory since the noise level is not selective in frequency, that is to say, the measurements taken by the analyzer were of the total average range and did not show predominant dynamic variations during each hour, which could serve as reference.

To avoid this obstacle the characteristics of the noise of the system were determined experimentally by use of a permanent magnet microphone with an output transformer coupled to a sound amplitude analyzer connected oscilloscope.

With the information afforded by the analyzer of sound magnitude and the oscilloscope, the next step was to measure the sound level and determine the changes which took place continuously during the 24 hours of the day. The main characteristics necessary in the equipment were:

a. Frequency selectivity at various amplitudes over the operation band.

b. Compatibility with present instrumentation in such a way that the sound signal could be registered or controlled.

c. High trustworthiness with the maintenance needs being infrequent.

It was found that the ideal equipment should comprise the following parts:

a. A permanent magnet microphone with output transformer.

b. A sound amplifier with a tone circuit for adjusting frequencies from 375 to 3300 Hz.

c. A signal converter which receives the output signal from the amplifier and gives a standard signal of 10–50 mA.

d. A voltage regulating source which supplies regulated voltages.

Once the sound amplitude measuring equipment is installed and continuously registers, we look for the existing relation between this measurement and the oven variables, as well as the characteristics of the raw material which feeds the oven.

For this case, statistical data of some variables such as the litre weight were taken, the saturation factor of limestone (LSF), the relationship of aluminum/iron (A/F) and put on graphs, some of which are shown on later figures (FIG. No. 6).

From the graphs, a close relationship was observed between the sound level and the liter weight, unlike the sound level and the characteristics of the raw material.

Even under conditions of marked instability in the oven, the sound signal "follows" the values obtained from the liter weight.

To get automatically the relationship which exists between the liter weight and the sound level the technique of lineal regression is used. It was assumed that the relationship between the liter weight and the sound level follows the general reasoning of the following equation:

$$Y = A_o + A_1 x$$

Where $A_o$ and $A_1$ are constants which must be found, and where Y is the sound level and X is the liter weight.

On the other hand, the forecasting capacity of this equation once the values of $A_o$ and $A_1$ are found (in spite of the experimental data), it is measured by the correlation coefficient R is defined by:

$$A - R = \frac{N \Sigma XY - (\Sigma X)(\Sigma Y)}{\sqrt{[(N \Sigma X^2 - (\Sigma X)^2][(N \Sigma Y^2 - (\Sigma Y)^2]}} A;$$

The correlation coefficient tells us the forecasting capacity of the equation, when this coefficient nears zero it may be showing us that the equation has little forecasting capacity and that there isn't much relationship between X and Y. Where the value of R nears ±1, the relationship between X and Y becomes narrower and the equation has more forecasting capacity.

$X_1$ — Coordinated X from the measuring points (liter weight).
$Y_1$ — Coordinated Y from the measuring points (sound level).
N — Number of measuring points.
R — Coefficient of correlation.
$A_0$, $A_1$ Coefficients of the regression line.

Using the computer which has been fed the experimental data, obtained during some stages of the operation of the oven, the following results were obtained:

| | $A_0$ | $A_1$ | R | (L/W) | MEAN (L/W) |
|---|---|---|---|---|---|
| 1 | 32.580 | 0.0321 | .6563 | 113.9 | 1273 |
| 2 | 41.812 | 0.0231 | .6961 | 49.5 | 1279 |
| 3 | 49.590 | 0.0180 | .7411 | 66.9 | 1186 |
| 4 | 74.350 | 0.0015 | .4568 | 44.3 | 1319 |
| 5 | 25.794 | 0.0380 | .8552 | 71.5 | 1254 |
| 6 | 38.740 | 0.0279 | .9131 | 132.5 | 1191 |

With the results obtained the following observations can be made:

The coefficient of correlation R is very close to +1, which means that the relationship between the liter weight and the sound amplitude is close.

From the experimental data with this variable the following results were obtained:

1. That it is possible to measure the sound amplitude of the satellite cooler.
2. The measure of sound amplitude is closely related to the liter weight, even the values of liter weight might go over the line of regression in some cases (caused perhaps by poor sampling of the material or by the effect of variables not yet determined).
3. The continuous measuring of this variable allows the operator to know the characteristic of the material which comes out of the oven, even without the need to observe it directly. On the other hand, in the case in which the oven load (oven current) does not openly show the gradual heating or cooling status of the oven, the sound signal acts as a guide during the operation even in the presence of the existing time delay between the material burning in the heat drying zone and that which goes through the cooler.
4. From the maintenance point of view, the measuring and calibration of the signal requires cleaning and gauging check-ups at periods of up to 4 months or more, so the check-ups may be programmed for preventive maintenance.

Other objectives, uses and advantages of the invention, will be found as the invention is described in detail.

The characteristic details of the present invention are clearly shown in the following description and in the accompanying drawings as an illustration wherein the same reference symbols are used to indicate the same parts in the various figures.

Figure 1:
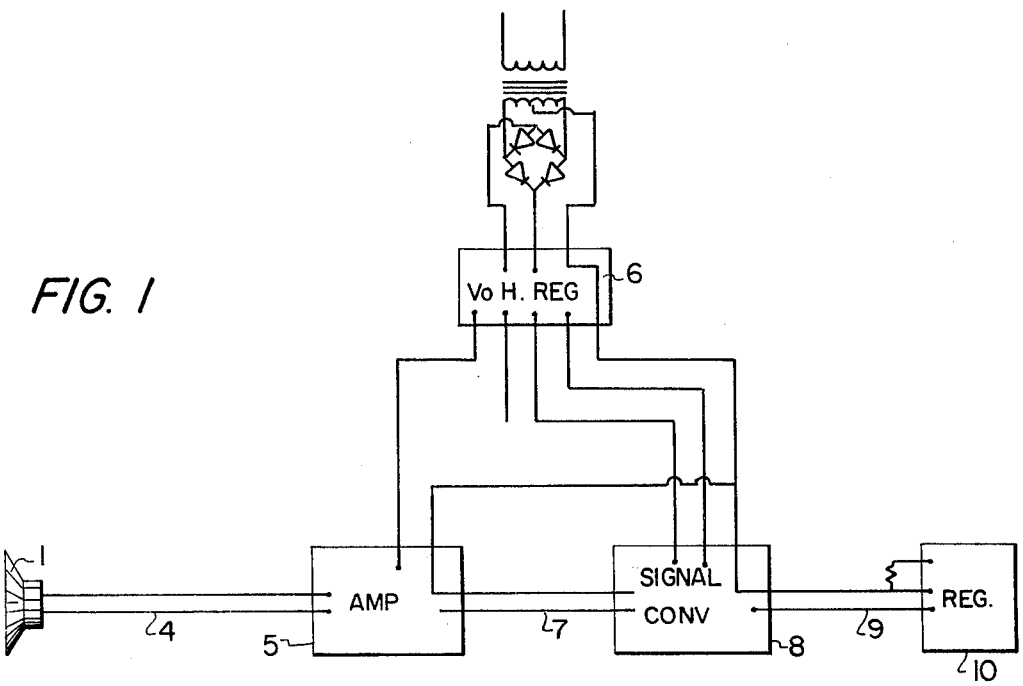
FIG. 1, shows a schematic block circuit diagram of the detection system or sound amplitude detector.
Figure 4:
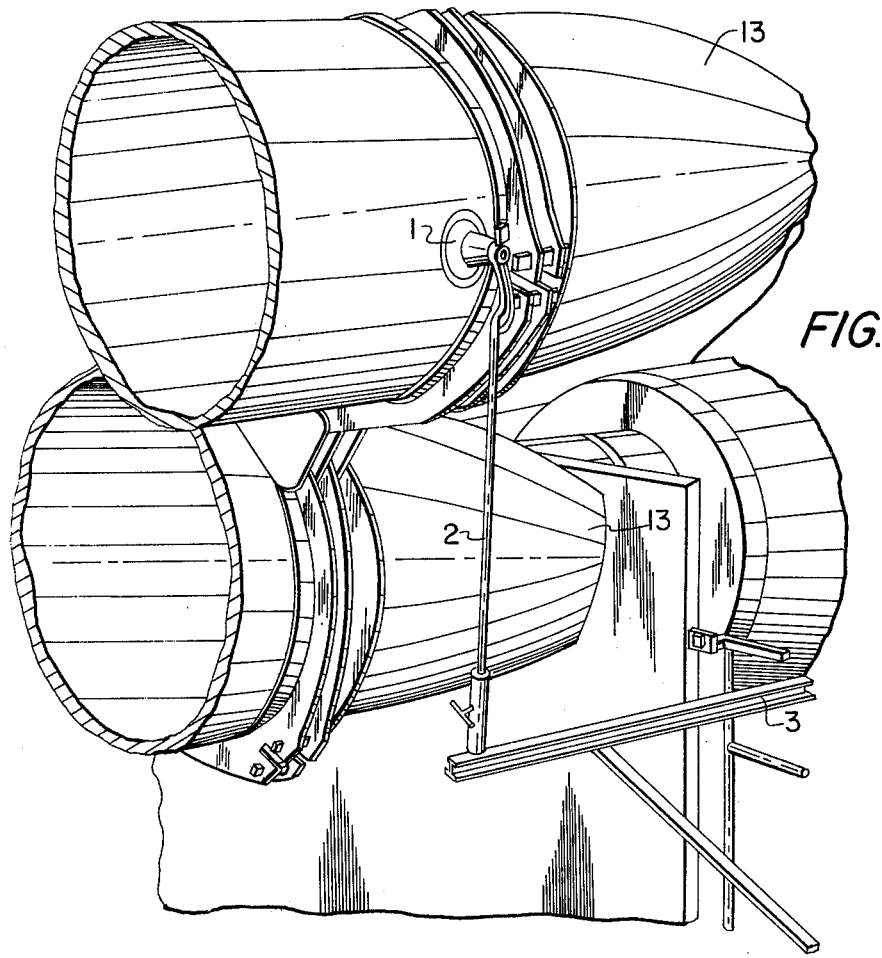
FIG. 4, shows a conventional view of one of the satellite sections and of the bar and post which support the microphone.

With reference to said figures, this system is characterized by the use of a permanent magnet microphone 1 which ought to be placed near the discharge pipes 12 which connect the rotative oven 11 to the satellites 13. The location of the microphone (1) at this point is important since it makes it possible to avoid noises external to the measuring such as from motors, fans, or any other apparatus nearby. Likewise, it is precisely at this point where the material just heat dryed 14 comes out and therefore where it is easier to determine its grade. It is therefore important to place the microphone 1 at approximately one meter from the discharge pipes 12 and for the purpose the microphone 1 ought to be placed on a post 2 which in turn is supported by a base 3.

The microphone 1, by means of a primary line 4 comprising a high temperature cable is able to withstand the conditions of the operation which as it passes to a cooler area may use Belden type cable with two conductors with mesh or wire as shielding to avoid insertion of unwanted signals to the measurements. The microphone is connected to the amplifier 5, which should preferably have a tone circuit to adjust frequencies from 375 to 3300 Hz and two gauge adjustments, one for sensitivity and one for output level selection. The sensitivity gauge allows the output signal from the amplifier 5 to be set at any value desired within the range of −1 to −5 VDC. Thus the liter weight corresponding to 50% of the graph is better determined, and optimum gauging conditions correspond to an output signal of −3 VDC. The adjustment knob ought to be anti-clockwise so that the output signal may vary directly with the changes of the input signal.

The amplifier 5 is connected to a signal converter 8 by means of a secondary line 7 with the following preferred characteristics in order that it may function at optimum conditions: capacity for the input signal of −1 to −5 VDC and output signal of 10 to 50 mA, in such a manner that this be adaptable to the majority of the instrumentations used to measure values in cement manufacture.

The signal converter 8 is connected by a third line 9 to a signal register 10 which for convenience in the operation ought to be mounted on the regular panels which are used in the oven and coolers' control section.

The amplifier 5 as well as the signal converter 8 receive the operation current from an alternating current line generally of 110 to 120 volts preferably from a voltage regulating source 6 which is connected to the regular alternating current line with outputs to the sound amplifier 5 as well as to the signal converter 8.

Figure 2:
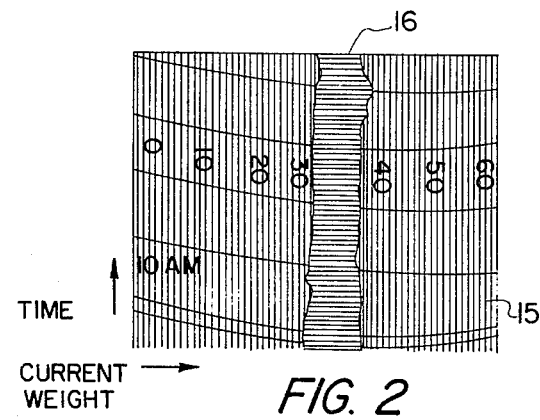
FIG. 2, shows a graph of the sound produced by the material in the satellite cooler.
Figure 3:
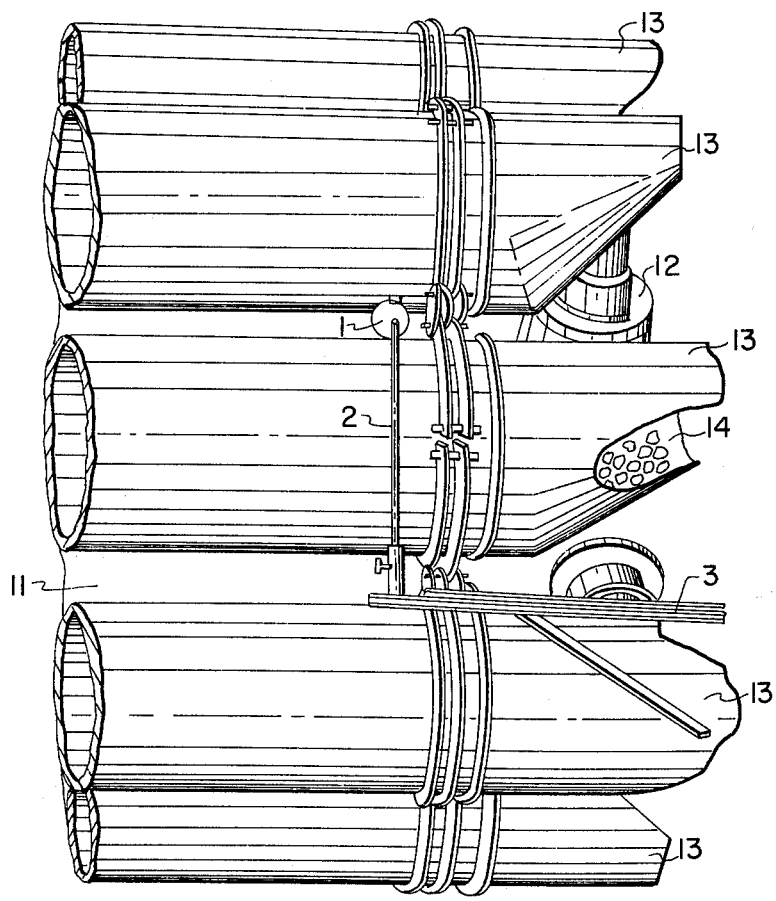
FIG. 3, shows a conventional view of the microphone mouned near the discharge pipes of the rotative oven to the satellite cooler.
Figure 5:
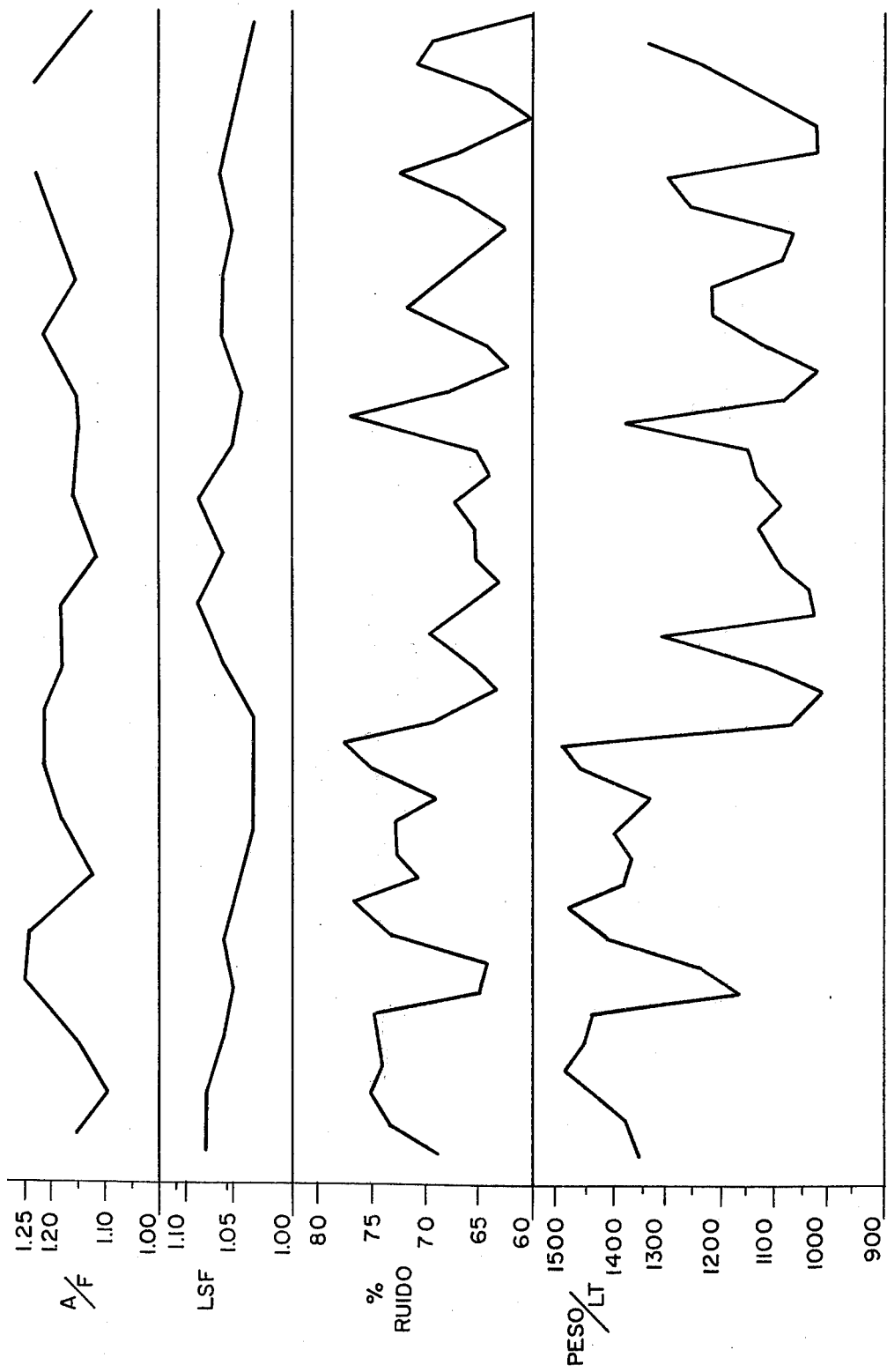
FIG. 5, shows a graph of the relationship between the changes occurred in the sound level and the liter weight during an unstable period in the oven.

The system detecting the sound of the heat dryed material 14 will function in the following manner: Once the material 14 has been heat dryed in the rotative oven 11 leaves through the discharge pipes 12 and passes to the satellites 13. Due to the consistency of the material 14 it hits the metallic walls of the discharge pipes 12 as well as of the satellites 13. The sound is received by the microphone 1 which sends it through the primary line 4 towards the amplifier 5. This in turn sends it through the secondary line 7 as a sound signal which may vary from −1 to −5 VDC to the signal converter (8), which changes the sound signal to an alternating current whose power may fluctuate from 10 to 50 mA. Said current passes through the third line 9 to the signal register 10 to activate the needle which prints on the graph roll 15 of FIG. 2 the graph 16 which will show the intensity of the sound produced by the heat dryed material 14.

It is important to point out that the intensity of the sound has a direct relationship to the good or bad quality of the heat dryed material 14 in its later use for the manufacture of cement. This makes it possible to determine the grade of the heat dryed material 14 or clinker which is passing from the rotative oven 11 to the satellites 13 and such grade may be detected at the same instant it passes through since the graph 16 will show the sound amplitude which the material 14 produced.

Only as a reference point it is important to note that a sharp sound corresponds to a good grade of the heat dryed material 14 or clinker and a dull sound corresponds to regular or bad grade heat dryed material 14 or clinker.

What is claimed is:

1. A system measuring the weight of materials such as clinkers which pass from an oven to a cooler through a discharge pipe by means of sound, comprising in combination, a microphone placed to determine sound amplitude of the materials passing through said discharge pipe from the oven to the cooler, a frequency selective amplifier, and output means coupled to the amplifier to display variations in sound amplitude to thereby indicate the weight of said materials.

2. A system as defined in claim 2 wherein the output means comprises a current converter and a graphical chart producing register operable to display changes in current magnitude as said weight.

3. A system as defined in claim 1 including mounting means for said microphone comprising a bracket holding said microphone at a distance of the order of one meter from said discharge pipe.

4. A system as defined in claim 1 wherein the amplifier has a selectively variable frequency response in the range 375 to 3300 Hz.

* * * * *